US006177072B1

(12) United States Patent
Tuzun et al.

(10) Patent No.: US 6,177,072 B1
(45) Date of Patent: Jan. 23, 2001

(54) SOY HYDROLYSATE AND USE IN INSECT CONTROL

(76) Inventors: Sadik Tuzun, 406 E. University Dr., Auburn, AL (US) 36830; Ismail Alp, Li man Mahellesi, Bogacayi Cad, 32 Sok No:32 /10, Antalya (TR)

(*) Notice: Under 35 U.S.C. 154(b), the term of this patent shall be extended for 0 days.

(21) Appl. No.: 09/095,161

(22) Filed: Jun. 10, 1998

(51) Int. Cl.[7] .......................... A01N 25/00; A01N 61/00; A01N 65/00

(52) U.S. Cl. .......................... 424/84; 424/94.1; 424/94.2; 424/94.21; 424/94.6; 424/94.63; 424/94.64; 424/94.65; 424/94.66; 424/195.1; 424/405; 424/DIG. 10; 426/1; 426/44; 426/46; 426/49; 426/52; 514/918; 514/919

(58) Field of Search .......................... 424/84, 94.1, 94.2, 424/94.21, 94.4, 94.6, 94.63, 94.64, 94.65, 94.66, 195.1, DIG. 10, 405; 426/1, 44, 46, 49, 52; 514/918, 919

(56) References Cited

U.S. PATENT DOCUMENTS

| | | | | |
|---|---|---|---|---|
| 3,689,277 | * | 9/1972 | Sfat et al. | 426/11 |
| 3,974,294 | * | 8/1976 | Schwille et al. | 426/32 |
| 5,274,079 | * | 12/1993 | Katayama et al. | 530/372 |
| 5,290,749 | * | 3/1994 | Christians et al. | 504/189 |

OTHER PUBLICATIONS

Grant & Hackh's Chemical Dictionary (5th Ed. 1987), pp. 213–215,321.*
CAB Abstracts: Cirio et al., "Fruit fly control by chemical attractants and repellents", *Bolletino del Laboratorio di Entomologia Agraria—"Filipo Silvestri"*, Portici (1980) 37:127–139.
Flath, et al., Alpha–Ionol as Attractant for Trapping *Bactrocera latifrons* (Diptera: Tephritidae), *J. Econ. Entomol.*, 87:1470–1476 (1994).
Reissig, W.H., Field Tests of Traps and Lures for the Apple Maggot, *J. Econ. Entomol* 67:484–486 (1974).
Loke et al., Semichemicals and Related Compounds in Insect Pest Management—Malaysian Experiences, Chapt. 9, *Pest Management and the Environment in 2000*, H.S. Barlow, Ed., CAB International, Wallingford, U.K., 111–126 (1992).
Section Ch, Week 197847, Derwent Publications Ltd., London, GB; Class D13, AN 1978–84574A XP002118896 & JP 53 118547 A (Ajinomoto KK), Oct. 17, 1978 (Oct. 17, 1978) abstract.
Teodorescu, Gheorghe RO: "Peptone for bacteriology from soybean oil manufacture wastes" retrieved from STN Database accession No. 108:201361 CA XP002118894 abstract & RO 92 025 B (Institutul Cantacuzino, Bucuresti, Rom.) Jul. 30, 1987 (Jul. 30, 1987).

Matsuyama, Eiichi: "Fruit–fly attractant" retrieved from STN Database accession No. 87:195563 CA XP002118895 abstract & JP 52 096741 A (Daiichi Noyaku K. K., Japan) Aug. 13, 1977 (Aug. 13, 1977).

Section Ch, Week 199808, Derwent Publications Ltd., London, GB; Class C07, AN 1998–080009 XP002118897 & JP 09 313083 A (Ishii H) Dec. 9, 1997 (Dec. 9, 1997) abstract.

Section Ch, Week 198114, Derwent Publications Ltd., London, GB; Class C03, AN 1981–24454D XP002118898 & JP 56 015204 A (Ryukyu Oil KK), Feb. 14, 1981 (Feb. 14, 1981), abstract.

Section Ch, Week 199240, Derwent Publications Ltd., London, GB; Class C07, An 1992–328081 XP002118899 & JP 04 235902 A (Tada S), Aug. 25, 1992 (Aug. 25, 1992) abstract.

Robacker, D.C., Specific Hunger in *Anastrepha ludens* (Diptera: Tephritidae): Effects on Attractiveness of Proteinaceous and Fruit–Derived Lures, *Environ. Entomol.* 20:1680–1686 (1991).

Heath et al., Systems to Monitor and suppress *Ceratitis Capitata* (Diptera: Tephritidae) Populations, *Florida Entomologist*, 79:144–153 (1996).

Epsky et al., Visual Cue and Chemical Cue Interactions in a Dry Trap with Food–Based Synthetic Attractant for *Ceratitis capitata* and *Anastrepha ludens* (Diptera: Tephritidae), *Environ. Entomol.*, 24:1387–1395 (1995).

Banham, F.L., An Evaluation of Traps for the Western Cherry Fruit Fly (Diptera: Tephritidae), *J. Entomol. Soc. British Columbia* 70:13–16 (1973).

Prokopy et al., Effect of Source and Condition of Animal Excrement on Attractiveness to Adults of *Ceratitis capitata* (Diptera: Tephritidae), *Environ. Entomol*, 22:453–458 (1993).

Nigg, et al., Age–Related Response of *Anastrepha suspensa* (Diptera: Tephritidae) to Protein Hydrolysate and Sucrose, *J. Econ. Entomol*, 88:669–677 (1995).

Reissig, W. H., Comparison of Traps and Lures for *Rhagoletis fausta* and *R. cingulata*, *J. Econ. Entomol.*, 69:639–643 (1976).

* cited by examiner

Primary Examiner—John Pak
Assistant Examiner—Frank Choi
(74) Attorney, Agent, or Firm—Dilworth & Barrese, LLP

(57) ABSTRACT

Soy hydrolysate compositions are produced by a process utilizing multiple enzymes. The soy hydrolysate compositions provide insect attractant and repellent properties. Methods of using the soy hydrolysate compositions for insect control are also disclosed.

18 Claims, 2 Drawing Sheets

SOY HYDROLYSATE AND USE IN INSECT CONTROL

BACKGROUND

1. Field of Invention

The invention relates generally to compositions for use as insect attractants/repellents and, more particularly, the insect specific control of economically important pests.

2. Description of Related Art

Insect pests are known to cause huge economic losses in agriculture. Certain infestations can decimate entire crop yields which can exert detrimental effects on entire economies. Fruit flies, which belong to the family of tephritidae, cause severe losses on many fruit trees including olive, citrus, peach, pear, fig, apricot and avocado. As a result, various methods of pest control have been developed to reduce such losses. Administration of toxic pesticides over large areas, while effective to reduce the number of pests, raises environmental concerns and can result in toxicity to consumers of fruit. Consequently, techniques which reduce or eliminate the negative environmental impact of pest control are highly desirable.

One strategy is to provide an insect lure which attracts and traps insects in the vicinity to allow a determination of exactly what insects are in the vicinity. In this manner, effective treatments may be devised for specific pests which are specific to those pests thus increasing the efficiency of pest control. Many field applications of lures use baited-traps and paintable sticky adhesives. See Epsky et al., *Environ. Entomol.*, 20:1680–1686 (1995); Heath et al., *Florida Entomologist* 79:144–153 (1996). In addition, an insect lure may be mixed with a pesticide such that insects are attracted to and come into contact with the pesticide, resulting in pest control. This technique avoids widespread dissemination of pesticides on fruits and crops.

Several protein hydrolysates, fruit juices, and synthetic chemicals have been reported to attract flies belonging the tephritidae family. See, e.g., Robacker, D. C., *Environ. Entomol.* 20:1680–1686 (1991); Epsky et al., *Environ. Entomol.* 24:1387–1395 (1995); Cirio et al., *Bolletino del Laboratorio di Entomologia Agraria "Filipo Silvestri"*, Portici 37:127–139 (1980). Examples of synthetic chemicals which attract fruit flies include trimedlure (1,1 di methyl-4 (and 5)-chloro-2-methyl-cyclohexane-l-carboxylate) and ionone- and ionol-related compounds, but the activity of the latter two compounds is specific to males. See Flath et al. *J. Econ. Entomol.* 87:1470–1476 (1994).

Certain commercially available protein hydrolysates, such as yeast hydrolysate and corn hydrolysate, are used as fruit fly attractants and are generally produced by acid hydrolysis or by enzymatic hydrolysis with trypsin. Protein hydrolysates provide a source of energy for flies, especially for females due to extra protein needed to mature their ova (Nigg et al., Age-related response of *Anastrepha suspensa* (Diptera:Tephritidae) to protein hydrolysate and sucrose, *J. Econ. Entomol.* 88:669–677 (1995). Solutions of ammonium salts and animal excrements as well as mixtures of various ammonium salts and commercial hydrolysates have also been reported to attract fruit flies. See Reissig, W. H., *J. Econ. Entomol.* 67:484–486 (1974); Reissig, W. H., *J. Econ. Entomol.* 69:6639–643 (1976); Propky et al. *Environ. Entomol.* 22:453–458 (1993); Epsky et al., *Environ. Entomol.* 20:1680–1686 (1995); Nigg et al. (1995), supra. NU-LURE™, is a commercially available standard lure made of corn protein hydrolysate, which has been used to trap flies belonging to Tephritidae. See Banham, F. L., *J. Entomol. Soc. British Columbia* 70:13–16 (1973); Loke et al., *Pest Management and the Environment in* 2000, H. S. Barlow, Ed., CAB International, Wallingford, U.K., 111–126 (1992); Flath et al., 1994 supra; Nigg et al. 1995 supra; Heath et al. 1996 supra. However, NU-LURE™ acts as a general attractant and lacks specificity against flies belonging to Tephritidae family. See Heath et al., supra.

Soy hydrolysates produced by acid hydrolysis are reported to have been used as attractants. A soy hydrolysate was reported to have limited activity as an attractant when used alone in Sectar traps, and was active only in the presence of 50% ammonium hydroxide (Reissig, *J. Econ. Entomol.* 67:484–486 (1974) Table 1; Reissig, *J. Econ. Entomol.* 69:639–643 (1976). Other studies indicate that acid hydrolyzed or trypsin digested soy extracts alone (i.e. without addition of 50% ammonium acetate) do not have sufficient activity to attract fruit flies. See Reissig, (1976) supra; Banham, supra; Reissig, (1974) supra. Soy lecithin and its chemical fractions are reported to have repellent activity against fruit flies belonging to Tephritidae (Cirio et al., supra). U.S. Pat. No. 4,160,824 describes insect attractive compositions containing acid-hydrolyzed defatted cereals which is indicated to be a more effective insect attractant than known acid-hydrolyzed soy bean cakes.

Existing protein hydrolysate lures are relatively expensive and are unsuited in economically depressed areas. There is a clear need for economic commercially available lures which have sufficient activity and target specific pests.

SUMMARY

The present invention provides a soy hydrolysate composition produced by a process including treating granulated and washed soy beans with lipase, protease and amylase under enzymatic conditions to produce a soy hydrolysate composition. Also provided are methods of using the composition as an insect attractant or insect repellent. Methods of killing insects by using the compositions described herein in combination with insecticide are also described.

Further provided is a process of making a soy hydrolysate including providing granulated soy beans; washing the granulated soy beans with water and isolating soy particles; mixing the soy particles with water; treating the soy particles/water mixture with enzymes including lipase, protease and amylase to produce a soy hydrolysate.

DETAILED DESCRIPTION OF PREFERRED EMBODIMENTS

Figure 1:
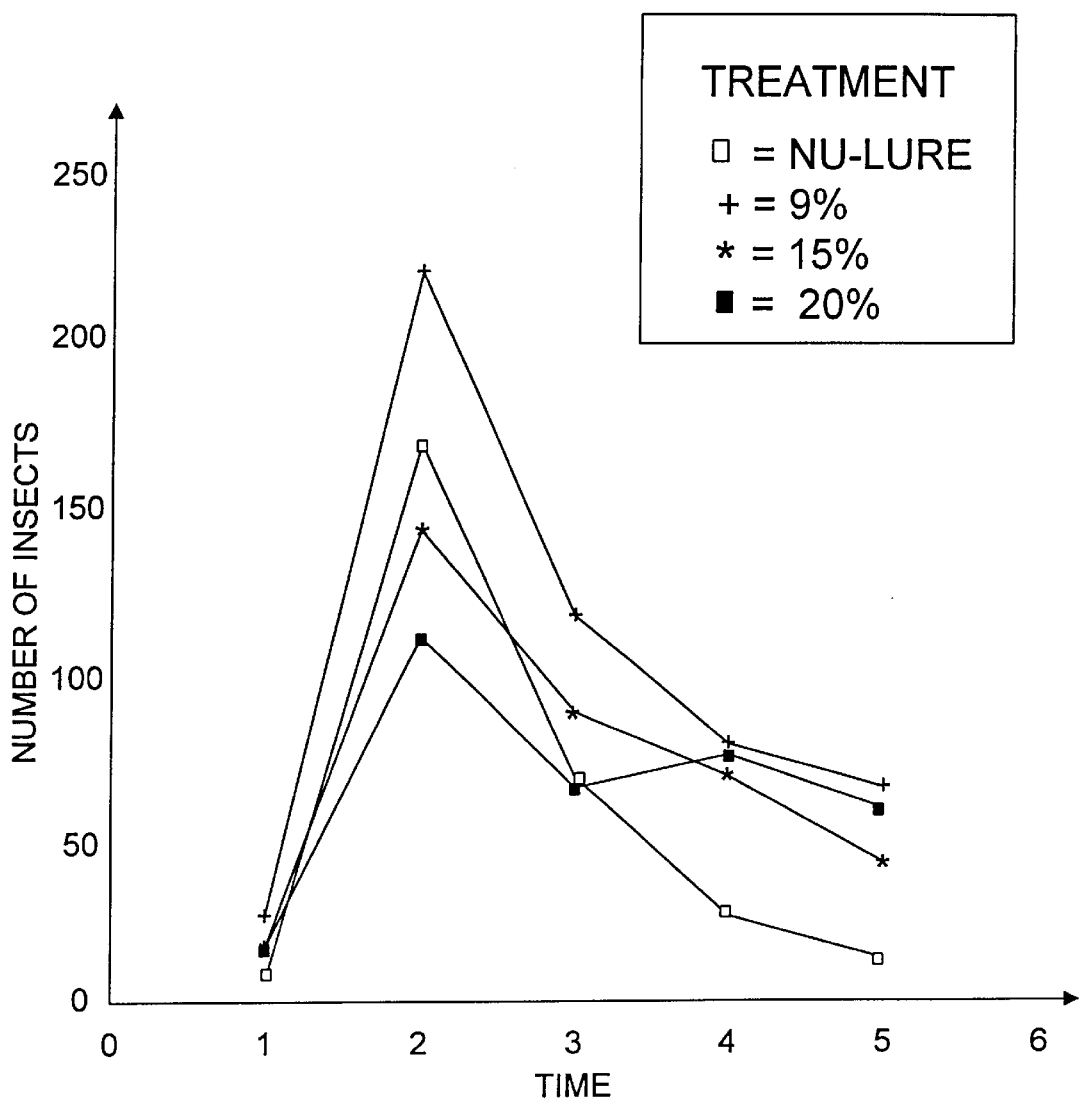
FIG. 1 is a graph showing relative attractive effects at different concentrations over time of various attractant compositions on female Mediterranean fruit flies.

The present invention involves soy hydrolysate compositions which attract certain insects and alternatively repel other insects. The insects specifically attracted by present compositions include some of the most economically important pests such as flies belonging to Tephritidae family, including *Bactyrocera oleae* (olive fruit fly) and *Ceratitis capitata* (Mediterranean fruit fly). Insects repelled by the present compositions include aphids. Accordingly, an insect attractant is provided which is a soy hydrolysate possessing significant attractive and repellant activity and specificity.

Soy hydrolysate compositions are provided in accordance with the present invention by grinding or otherwise granulating soy beans into particles. Any comminution method known to those skilled in the art may be used herein, e.g., milling, trituration and the like. Preferably, the particles range in size from about 0.5 mm to about 1.5 mm, more preferably above 0.7 mm.

The soy particles are mixed with water to form a suspension that will settle upon standing. Particles which have been too finely ground will remain suspended and present difficulties in further processing. The amount of soy particles and water used is not critical and can range, e.g., from a particle to water weight ratio of 1:20 to 10:1, preferably from about 1:10 to about 4:1. Thus, in particularly useful embodiments, approximately 400–1500 gms of soy particles are mixed with about 4 liters of water. When the suspension settles, the supernatant, which contains mostly starch, is decanted. The remaining pellet is resuspended in water and again allowed to settle. This washing process should be conducted at least two times and repeated until the supernatant is clear.

The resulting soy particles are mixed with water and treated with enzymes. Multiple enzymes are used to digest the soy. A suitable combination of enzymes includes at least amylase, lipase and protease. The combined activity of the enzymes catalyzes protein, lipid and starch contained in the soy particles into smaller molecules such as sugars and fatty acids to form a soy hydrolysate composition especially attractive to Tephritidae.

The enzyme treatment is carried out under enzymatic conditions. Suitable enzymatic conditions are temperatures of about 25 to about 45° C. and a pH ranging from about 4 to about 8. If the pH of the enzymatic reaction mixture drops below about pH 4.3 it can be adjusted upwards with a buffer. The amount of lipase used to treat the soy particles ranges from about 20,000 to about 45,000 units, preferably from about 30,000 to 40,000 units, most preferably about 37,500 units. The amount amylase used to treat the soy particles ranges from about 15,000 to about 50,000 units, preferably from about 25,000 to 40,000 units, most preferably about 33,000 units. The amount of protease ranges from about 1,200 to about 4,500 units, preferably from about 2,000 to 3,000 units, most preferably about 2,400 units. Proteases which are useful herein cleave peptide bonds or otherwise provide peptides derived from larger proteins. Useful proteases include pepsin, peptidase, trypsin, proteinase A and proteinase K. A preferred protease mixture is commercially available from Sigma Company, St. Louis, Mo., under the designation Protease Type I from Bovine Pancreas, Catalog #P0384.

Soy hydrolysate compositions produced by the methods described herein may optionally be diluted with water. The concentration of the soy hydrolysate composition should be at least about 1% to 100% in an aqueous solution and is preferably about 5% to about 20% volume/volume solution in water. The soy hydrolysate compositions and solutions thereof have high and specific activity against fruit flies belonging to Tephritidae family. A ten percent solution of a soy hydrolysate composition according to the present invention in baiting jars attracted>25 fruit flies from the nearest host plant present at a distance of at least 150 meters within an hour, compared to <5 fruit flies trapped in jars containing a previously known attractant (NU-LURE™) placed only 1 meter away from baiting jars containing the present compositions.

Unlike previously known protein hydrolysate-based lures which are sweet smelling, soy hydrolysate compositions of the present invention normally have an unpleasant odor that disappears within about an hour after spraying. The soy hydrolysate compositions produced in accordance with the preferred methods described herein are clear liquids with slightly yellowish color and a pH of about 6.8. Previously known protein hydrolysate based lures have acidic pH's (4.0–4.5). Total nitrogen in the preferred soy hydrolysate compositions is about 0.0624% (measured by Kjedhal method). About 3.9% of the preferred soy hydrolysate composition is proteinaceous material. The preferred soy hydrolysate compositions contain about 515 ppm ammonia. About 506 ppm of this amount is in bound state as ammonium ion and about 9 ppm is dissolved free ammonia at the neutral pH. When the present compositions are used as 9–10% solution of the soy hydrolysate in water, the amount of dissolved free ammonia is normally too small to have any appreciable contribution to attractant activity. There is also a positive reaction with Kovacs test indicating the presence of an indol ring in the solution.

The soy hydrolysate compositions can be applied in baiting jars or combined with insecticides. Suitable insecticides include DDT (dichlorodiphenyltrichloroethane), methoxychlor (2,2'-bis(4-methoxyphenyl)-1,1,1-trichloroethane), lindane (gamma isomer of hexachlorocyclohexane), chlordane (octachlorohexahydromethanoindene), aldrin (endo hexachlorohexahydrodimethanonaphthalene), toxaphene, ethion (O,O,O',O'-tetraethyl-S,S'-methylenedithiophoshate), parathion (O,O-diethyl-O-paranitrophenyl thiophosphate), phosalone (O,O-diethyl-3-dithiophosporyl-methyl-6-chlorobenzoxazolone), sevin (1-naphtyl N-methylcarbamate), carbofuran (dimethyldihydrobenzofuryl N-methylcarbamate), malathione (diethyl mercaptrosuccinate, S-ester with 0,0-dimethyl phosphorodithioate), decamethrin (alpha-cyanophenoxybenzyl dibromovinyl-dimethylcyclopropane-carboxylate), cypermethrin (phenoxybenzyl cis-transdimethyldichlorovinylcyclopropane-carboxylate), and fenvalerate (alpha-cyanophenoxybenzyl chlorphenyl-methylbutylbutyrate), for example.

For effectiveness, only a portion of the trees, for example, approximately 1 to 1½ m$^2$ of the trees or less, need to be treated. The soy hydrolysate compositions may be used as a bait in traps to determine insect populations as a part of an insect management strategy. The compositions of the present invention can also be used for spot application on fruit trees in combination with insecticides. Any method of application known to those with skill in the art including spraying or painting can be used to apply the soy hydrolysate compositions described herein. The present compositions are relatively inexpensive since about 1000 gr (4 liter) of the preferred soy-product produced herein will be sufficient to spot spray 400 trees.

Soy hydrolysate compositions according to the present invention may remain active for 6 months or more without addition of any protectants when stored in a refrigerator. Activity remains for at least two weeks when the compositions are placed into baiting jars and during the full duration of application with an insecticide (e.g., malathione) in field studies. Addition of 0.125% ammonium hydroxide to the soy hydrolysate compositions results in coagulation of the proteins, with solids settling at the bottom of the container. The solution which separates from the solids typically has less than 50% of the activity; however, it should remain active for about 3 years when stored in a refrigerator. Autoclaving may be employed to increase stability of the product.

In another aspect of the present invention, the soy hydrolysate compositions produced in accordance with the methods described herein were surprisingly found to function as an insect repellent against certain insects such as aphids.

In yet another aspect of the present invention, the soy hydrolysate compositions are modified to include additional ingredients which can change the specificity from one particular species of insect, or family of insects to another particular species or family of insects. For example, in one embodiment, the addition of brewers yeast converts properties of the present compositions to attract lepidopteran insects such as butterflies. The lepidopterans are among the most important pests of plants, especially in storage.

In comparison tests, the soy hydrolysate compositions described herein were approximately twice as effective as the widely-used commercial product NU-LURE™ (Miller Chemical and Fertilizer Co. Box 333, Hannover, Pa. 17331) at the same concentrations (9% solution recommended for NU-LURE™). NU-LURE™ also attracts flying insects non-specifically since only 10–20% of the total number of flies trapped in a baiting jar containing NU-LURE™ belonged to the family Tephritidae, compared to 70–90% in baiting jars containing the present soy hydrolysate compositions. The present compositions at high concentrations (20% or greater concentration in water) also attracts other flying insects. The activity of NU-LURE™ in a baiting jars lasted about 3–4 days, whereas the present compositions were active in catching flies until 14 days after placing the baiting jars in the field as indicated by the presence of live flies in the baiting jars.

The following examples are provided for purposes of illustrating certain aspects of the present invention and should not be construed as limiting the scope of the invention.

EXAMPLE 1

Production of Soy Hydrolysate

Finely granulated soy particles (capable of passing through U.S. standard sieve No. 14) was washed with water (55–60° C.), repeatedly as follows: approximately 4 liters of water was poured into a container having about 1000 grams of finely granulated soy particles. The container was left for settling and supernatant subsequently removed carefully by siphoning. At least 4 liters of water (55–60° C.) was poured inside the container having the soy particles in pellet form, the container shaken and allowed to settle. The supernatant was removed again. The procedure was repeated until the supernatant became completely clear.

The remaining soy particles were dissolved in 5 liters of water at room temperature. The enzymes used for digestion of the soy particles and their preferred concentrations were as follows: lipase 37,500 units; protease 2,400 units (Type I, Crude From Bovine Pancreas, Sigma Cat. #P0384, commercially available from Sigma Corp.); and amylase 33,000 units. The pH of the solution at the beginning of the enzymatic digestion was approximately 7.0 (the preferred pH for enzymatic reaction).

The enzyme-soy particle mixture was incubated in an incubator at 35–40° C. for 24 hrs. When the pH of the solution dropped to about 4.3, it was adjusted to about 7.0 by the addition of sodium bicarbonate. The mixture was then incubated 24 additional hours. The pH of the final product was approximately 6.8. While the solution resulting from first incubation has some activity, maximum activity is obtained after the second enzymatic reaction.

EXAMPLE 2

Production of Soy Hydrolysate

The same procedures were followed as for Example 1 above, with the exception that a different combination of enzymes was used as follows:

| | |
|---|---|
| Pancreatin | 1,200 µg |
| Bromelain | 150 µg |
| Lipase | 37,500 units |
| Protease | 2,400 units |
| Amylase | 33,000 units |

EXAMPLE 3

Field Tests to Demonstrate the Activity of Soy Hydrolysate

A. Baiting jar experiments

Field studies were conducted over a two year period in an orange grove containing 800 trees located at Aksu, Antalya, Turkey. 15 cm diameter baiting jars (IPS systems Inc.) were filled with 300 cc of 9, 15 and 20% v/v water solutions of the soy hydrolysate according to the present invention. For comparison purposes, NU-LURE™ was used as recommended (9% v/v solution). Five baiting jars were used per treatment and the jars containing various concentrations of the present compositions and NU-LURE™ were placed randomly, at least 20 meters away from each other, in order to avoid preference for a particular attractant. When jars were placed near each other, fruit flies were preferentially attracted to the soy hydrolysate compositions. The experiments were designed in complete randomized design and repeated over 5 week periods. The number of *Ceratitis capitata* in each jar was counted at weekly intervals and the solution was replaced with a fresh one. During the first year, infestation with fruit flies were rather low due to environmental conditions, although a 9% soy hydrolysate solution attracted the most flies. During the growing season of the second year, the natural populations of fruit flies were rather high and 9% solution of the soy hydrolysate compositions attracted more flies than NU-LURE™ in each experimental period with significant differences ($p \leq 0.05$) in most weekly counting periods. At week two, although 30% more (mean number) female fruit flies were counted in the jars containing 9% soy hydrolysate, the differences were not significant due to high variation. The data from these experiments is presented in FIGS. 1 and 2, and summarized in Table 1.

TABLE 1

Comparison of three concentrations of the Soy Hydrolysate Compositions with NU-LURE ™ over 5-week period during the growing season of orange fruit.*

| TREATMENT | FEMALE | MALE | FEMALE | MALE | FEMALE | MALE | FEMALE | MALE | FEMALE | MALE |
|---|---|---|---|---|---|---|---|---|---|---|
| 9% Compositions | 26.4A | 10.0A | 215.4A | 52.6A | 112.2A | 24.4A | 77.6A | 16.4A | 64.6A | 14.0AB |
| 15% Compositions | 18.6AB | 7.2AB | 135.0A | 45.8AB | 82.2AB | 19.8AB | 73.8A | 17.4A | 41.0AB | 9.2AB |
| 20% Compositions | 17.6AB | 8.8A | 103.8A | 36.0B | 59.0B | 17.4AB | 66.4A | 17.6A | 56.0A | 15.6A |
| 9% Nu-Lure ™ | 7.3B | 2.7B | 161.6A | 33.6B | 62.8B | 12.8B | 31.8B | 9.0B | 17.4B | 5.4B |

*Numbers indicate the mean number of Mediterranean fruit files collected in 5 baiting jars per treatment per time period. For each time period and sex (columns) means followed by the same letter are not significantly different. (P $\leq$ 0.05) according to Duncan's multiple range test.

Figure 2:
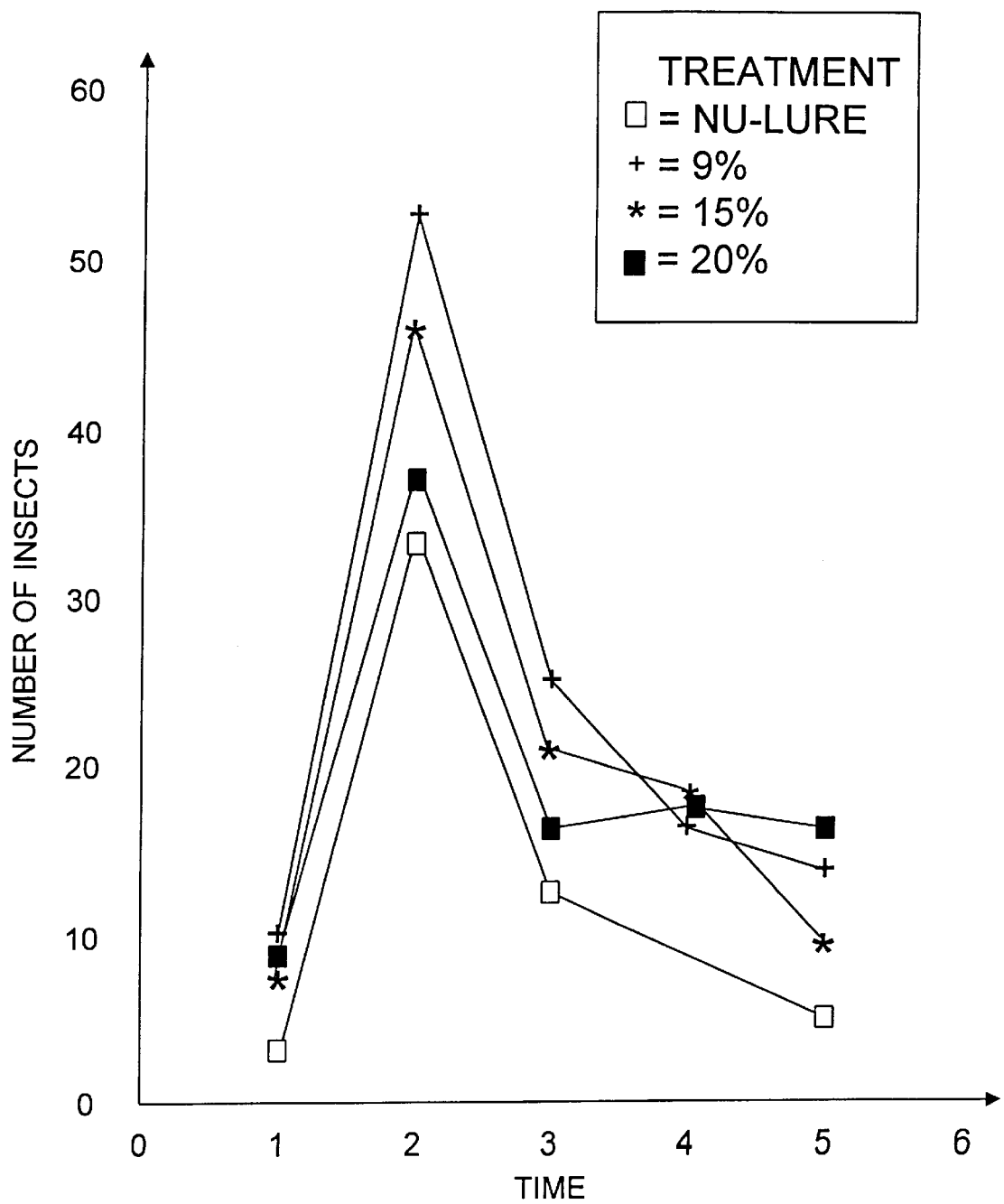
FIG. 2 is a graph showing relative attractive effects at different concentrations over time of various attractant compositions on male Mediterranean fruit flies.

In FIG. 1, the effect of different soy hydrolysate concentrations (9–20%) on the attraction of females of Mediterranean fruit flies, and comparison of their activity with commercial concentration of NU-LURE™ is presented. Time indicates weekly counting of female fruit flies. FIG. 2 is identical to FIG. 1 except that the Mediterranean fruit flies are male.

Overall, in all other time periods, 3–4 times more mean number of fruit flies were counted in the jars containing the 9% soy hydrolysate compared to NU-LURE™. At the end of the experimental period, the jars containing 9, 15 and 20% of soy hydrolysate compositions had a total of 3100, 2400 and 2100 *Ceratitis capitata*, respectively, whereas 9% solution of NuLure™ had 1700 *C. capitata*. Mean number of Mediterranean fruit flies collected throughout the experimental period in the baiting jars containing the 9% solution of soy hydrolysate was significantly different ($p \leq 0.05$) from the Mediterranean fruit flies collected in the jars containing 9% solution of NU-LURE™ (5% LSD). All treatments attracted an average of 80% females and 20% males. In every experiment, 70–90% of the total insects trapped in the baiting jars containing soy hydrolysate compositions were Mediterranean fruit flies whereas only 10–20% in the jars containing NU-LURE™. In another study, conducted during a different growing season, a soy hydrosylate according to Example 1 attracted a mean number of 198 Mediterranean fruit flies in a day compared to 84 with NU-LURE™ (significantly different $p \leq 0.05$).

Several studies conducted with *Bactrocera oleae* (olive fruit fly) and *Bactrocera dorsalis* (oriental fruit fly) indicated that the baiting jars containing 9% solution of soy hydrolysate also attracted at least twice as many of these fruit flies as NU-LURE™. *Bactrocera cucurbitae* (melon fly) was equally attracted by 5 NU-LURE™ indicating broad spectrum of activity within tephritidae family by the present soy hydrolysate. Moreover, specificity was also evident.

B. Spot spray applications containing insecticide I.

These studies were conducted at a field of *Diospyros khaki* which is the most susceptible host to *C. capitata*. Since the fruits have rather thin skin, damage caused by a single fly infestation basically destroys the market value of the fruit. A row of trees were spot sprayed with 5% solution of soy hydrolysate containing 4% Malathione insecticide. The spraying schedule included weekly sprays for a total 12 weeks. The yield was obtained from 5 trees randomly selected per treatment and each fruit was visually inspected for the presence of fly damage and the presence of fruit fly eggs. Fruits obtained from the trees treated with soy hydrolysate plus malathione had 95% of the fruits free of fly damage whereas control plots without insecticide treatment had total loss of fruit. The trees treated with weekly application of the insecticide DIPTEREX, an insecticide recommended for fruit fly control, as applied to cover whole tree, had 80% of the fruits free of fly damage. Trees treated with 4% malithione alone were found to have infestation of over 60% of the fruit. Fruit was harvested separately from each plot and the quality and marketability was assessed by the purchasers. The fruit obtained from plots treated with soy hydrolysate plus malathione was rated as the best and sold with the highest price.

The number of flies in each plot was determined by 5 baiting jars randomly placed in each plot. The mean number of insects collected in the plots spot sprayed with soy hydrolysate plus malathione was 64 whereas 190 Mediterranean fruit flies were collected in the plots treated with Dipterex indicating that more flies were killed with the treatment with soy hydrolysate plus malathione compared to DIPTEREX insecticide treatment.

Spot Spray Applications Containing Insecticide II

The test was conducted in an orange grove containing 1200 trees. 1½ m² of every other tree was sprayed with 3–4% soy hydrolysate with 4% malathione by 10 weekly intervals during the growing season. Control plants were either non-treated or treated with a recommended dose of DIPTEREX by spraying every single tree at I 0-day intervals (complete coverage). At the end of the experiment 10 trees were randomly chosen, and each fruit was inspected for the presence or absence of fruit fly damage. Soy hydrolysate and malathione treatment had 3% of the total fruit with fly damage whereas 10% with DIPTEREX treatment and 60% without any treatment had fruit fly damage. Soy traps were placed in several locations in the fields to determine fruit fly activity during the growing season. The number of flies trapped by the soy hydrolysate and malathione treated field was at least 20 fold less than the ones counted in diazinon treated fields.

EXAMPLE 4

The Activity of Soy Hydrolysate against Aphids

The soy hydrolysate compositions according to the present invention can be used as an insect repellent. To exemplify this, a ¹/₁₀ dilution solution was sprayed on the tobacco plants used to raise green peach aphids for experimental purposes, grown in a green house, daily for three days to actually provide additional food source for aphids. Surprisingly, all the plants sprayed were free of aphids within a week. Since number of dead aphids were negligible, it is apparent that the present compositions repel insects such as aphids.

EXAMPLE 5

Modification of the Soy Hydrolysate Compositions to Attract Lepidopteran Insects The soy hydrolysate compositions are capable of attracting lepidopteran insects such as butterflies by the addition of 25% w/v sugar and 1 tablespoon brewers yeast (Saccharomyces cerevisiae) into 5 L of solution containing the present compositions. The mixture is fermented at 30° C. for 48 hrs. Yeast provides additional vitamins such as folic acid and vitamin B as well as provides invertase activity to degrade sucrose into glucose and fructose. This preparation attracted numerous butterflies to the baiting jars, but did not completely destroy activity to attract fruit flies. Thus it is possible to broaden the range of activity, or modify insect specificity, by changing the ingredients of the basic preparation and enzymatic processes.

COMPARATIVE EXAMPLE 1

Acid hydrolysis of soy meal resulted in separation of oil and the final product did not have the characteristic smell of the present compositions and a solution obtained with acid hydrolysis has minimal activity. Also, trypsin digestion did not result in a product that is as active as the present compositions. Thus, the current techniques described above indicate that soy protein hydrolysates in commercially available forms are not active, confirming the results of others (Reissig 1974, supra, and 1976 supra). Although the smell of the soy hydrolysate compositions of the present invention is very different from other lures, i.e. NU-LURE™ has a sweet smell, the present compositions attract fruit flies more efficiently, indicating that the chemical components which attract flies are rather different. Moreover, the very high specificity to attract fruit flies further indicates that the chemical constituents of the present compositions are different than those of other lures.

It should be understood that modifications can be made to the embodiments disclosed herein. Therefore the above description should not be construed as limiting, but merely as exemplification of preferred embodiments. Those skilled in the art will envision other modifications within the scope of the claims appended hereto.

What is claimed is:

1. A soy hydrolysate composition produced by a process comprising:
   (i) washing soy particles with water to form a suspension that will settle upon standing leaving a supernatant and settled soy particles;
   (ii) decanting the supernatant from the settled suspension;
   (iii) repeating steps (i) and (ii) until the supernatant is clear; and
   (iv) collecting the resulting washed soy particles and treating said washed soy particles with a sufficient amount of a combination of enzymes including lipase, protease and amylase to produce a clear liquid soy hydrolysate composition having a slight yellowish color, an unpleasant odor and a pH of about 6.8, wherein the enzymatic treatment step is carried out in a pH range of about 4 to 8.

2. The soy hydrolysate composition according to claim 1 wherein the amount of lipase is about 20,000 to about 45,000 units; the protease is about 1,200 to about 4,500 units and the amount of amylase is about 15,000 to about 50,000 units.

3. The soy hydrolysate composition according to claim 2 wherein the amount of lipase is about 37,500 units; the amount of protease is about 2,400 units and the amount of amylase is about 33,000 units.

4. The soy hyrolysate composition according to claim 1 wherein the protease includes a combination of pepsin, trypsin, proteinase A and proteinase K.

5. The soy hydrolysate composition according to claim 1 further comprising sugar and brewers yeast.

6. The soy hydrolysate composition according to claim 1 further comprising an insecticide.

7. The soy hydrolysate composition according to claim 1 wherein the combination of enzymes further includes one or both of pancreatin and bromelain.

8. A method of attracting insects which comprises exposing the insects to an effective attracting amount of the soy hydrolysate composition of claim 1, with the proviso that said insects are not aphids.

9. The method of attracting insects according to claim 8 wherein the amount of lipase is from about 20,000 to about 45,000 units, the amount of amylase is from about 15,000 to about 50,000 unit and the amount of protease is from about 1,200 to about 4,500 units.

10. The method of attracting insects according to claim 9 wherein the amount of lipase is about 37,500 units, the amount of protease is about 2,400 units and the amount of amylase is about 33,000 units.

11. The method of attracting insects according to claim 8 wherein the soy hydrolysate composition further includes sugar and brewers yeast.

12. The method of attracting insects according to claim 8 wherein the insects are Tephritidae.

13. A method of killing insects which comprises exposing the insects to an effective attracting amount of the soy hydrolysate composition of claim 1, with the proviso that said insects are not aphids, the composition further including an effective insect killing amount of an insecticide.

14. A method of repelling insects which comprises exposing aphids to an effective repelling amount of the soy hydrolysate composition of claim 1.

15. A process of making a soy hydrolysate composition comprising:
   (i) washing soy particles with water to form a suspension that will settle upon standing leaving a supernatant and settled soy particles;
   (ii) decanting the supernatant from the settled suspension;
   (iii) repeating steps (i) and (ii) until the supernatant is clear; and
   (iv) collecting the resulting washed soy particles and treating said washed soy particles with a sufficient amount of a combination of enzymes including lipase, protease and amylase to produce a clear liquid soy hydrolysate composition having a slight yellowish color, an unpleasant odor and a pH of about 6.8, wherein the enzymatic treatment step is carried out in a pH range of about 4 to 8.

16. The process of making a soy hydrolysate according to claim 15 wherein the amount of lipase is about 20,000 to about 45,000 units; the amount of protease is about 1,200 to about 4,500 units and the amount of amylase is about 15,000 to about 50,000 units.

17. The process of making a soy hydrolysate according to claim 16 wherein the amount of lipase is about 37,500 units; the amount of protease is about 2,400 units and the amount of amylase is about 33,000 units.

18. The process of making a soy hydrolysate according to claim 15 wherein the soy particles range in size from about 0.5 to about 1.4 mm.

* * * * *